(12) United States Patent
Christiansen et al.

(10) Patent No.: US 12,303,104 B2
(45) Date of Patent: May 20, 2025

(54) SHEATH FOR A TIP OF A SCANNING DEVICE AND SYSTEM THEREOF

(71) Applicant: 3SHAPE A/S, Copenhagen K (DK)

(72) Inventors: Alexander Bruun Christiansen, Copenhagen Ø (DK); Pétur Gordon Hermannsson, Gentofte (DK); Søren Greve Jensen, Copenhagen S (DK); Mike Van Der Poel, Rødovre (DK)

(73) Assignee: 3SHAPE A/S, Kobenhavn K (DK)

( * ) Notice: Subject to any disclaimer, the term of this patent is extended or adjusted under 35 U.S.C. 154(b) by 719 days.

(21) Appl. No.: 17/275,441

(22) PCT Filed: Sep. 9, 2019

(86) PCT No.: PCT/EP2019/073972
§ 371 (c)(1),
(2) Date: Mar. 11, 2021

(87) PCT Pub. No.: WO2020/053136
PCT Pub. Date: Mar. 19, 2020

(65) Prior Publication Data
US 2022/0079426 A1    Mar. 17, 2022

(30) Foreign Application Priority Data
Sep. 12, 2018 (EP) .................... 18194075

(51) Int. Cl.
*A61B 1/00* (2006.01)
*A61B 1/227* (2006.01)
(Continued)

(52) U.S. Cl.
CPC ...... *A61B 1/00142* (2013.01); *A61B 1/00096* (2013.01); *A61B 1/0011* (2013.01);
(Continued)

(58) Field of Classification Search
CPC ............ A61B 1/00142; A61B 1/00096; A61B 1/0011; A61B 1/24; A61B 1/227;
(Continued)

(56) References Cited

U.S. PATENT DOCUMENTS

| | | | |
|---|---|---|---|
| 6,190,309 B1 | 2/2001 | Ooshima et al. |
| 6,468,076 B2 | 10/2002 | Kawamura |

(Continued)

FOREIGN PATENT DOCUMENTS

| | | | |
|---|---|---|---|
| CN | 101163453 A | 4/2008 |
| CN | 102228377 A | 11/2011 |

(Continued)

OTHER PUBLICATIONS

The extended European Search Report issued on Feb. 28, 2019, by the European Patent Office in corresponding European Application No. 18194075.0. (7 pages).

(Continued)

*Primary Examiner* — Michael E Teitelbaum
(74) *Attorney, Agent, or Firm* — Buchanan Ingersoll & Rooney PC

(57) ABSTRACT

A sheath for an intraoral scanning tip, where polarization is not substantially altered during scanning.

20 Claims, 11 Drawing Sheets

(51) Int. Cl.
*A61B 1/24* (2006.01)
*A61B 5/00* (2006.01)
*A61C 9/00* (2006.01)

(52) U.S. Cl.
CPC ................ *A61B 1/24* (2013.01); *A61B 1/227* (2013.01); *A61B 5/0086* (2013.01); *A61C 9/0053* (2013.01)

(58) Field of Classification Search
CPC .............. A61B 5/0086; A61B 1/00101; A61B 1/00179; A61B 1/00103; A61B 1/00135; A61C 9/0053; A61C 1/16
See application file for complete search history.

(56) References Cited

U.S. PATENT DOCUMENTS

| | | | |
|---|---|---|---|
| 6,549,794 B1* | 4/2003 | Nadeau, Jr. | A61B 5/0084 359/511 |
| 6,599,238 B2 | 7/2003 | Ooshima et al. | |
| 9,506,808 B2 | 11/2016 | Jeon et al. | |
| 10,251,558 B2 | 4/2019 | Sumi et al. | |
| 2003/0107652 A1* | 6/2003 | Williams | A61B 1/042 348/E5.025 |
| 2005/0283058 A1 | 12/2005 | Choo-Smith et al. | |
| 2007/0260231 A1 | 11/2007 | Johnston et al. | |
| 2009/0147373 A1 | 6/2009 | Rolland et al. | |
| 2012/0010468 A1 | 1/2012 | Afridi | |
| 2012/0040305 A1* | 2/2012 | Karazivan | A61B 1/00087 433/29 |
| 2012/0232406 A1 | 9/2012 | Zuluaga et al. | |
| 2013/0141558 A1 | 6/2013 | Jeon et al. | |
| 2014/0272766 A1 | 9/2014 | Andreiko et al. | |
| 2015/0230882 A1 | 8/2015 | Miller | |
| 2016/0213250 A1 | 7/2016 | Su | |
| 2016/0223714 A1 | 8/2016 | Ujihara et al. | |
| 2016/0367120 A1* | 12/2016 | Dupont | A61B 1/015 |
| 2017/0290492 A1 | 10/2017 | Hamm et al. | |
| 2018/0206940 A1 | 7/2018 | Kopelman et al. | |
| 2023/0389778 A1 | 12/2023 | Christiansen et al. | |

FOREIGN PATENT DOCUMENTS

| | | |
|---|---|---|
| EP | 1692995 A1 | 8/2006 |
| JP | H08146307 A | 6/1996 |
| JP | H11192207 A | 7/1999 |
| JP | 2001212161 A | 8/2001 |
| JP | 2008302233 A | 12/2008 |
| JP | 2013526702 A | 6/2013 |
| WO | 03051184 A1 | 6/2003 |
| WO | 2014013950 A1 | 1/2014 |

OTHER PUBLICATIONS

First Office Action issued on Dec. 1, 2023, by the Chinese Patent Office in corresponding Chinese Patent Application No. 201980074209. 3, and an English Translation of the Office Action. (25 pages).

Office Action (Notice of Reasons for Refusal) issued on Jun. 20, 2023, by the Japanese Patent Office in corresponding Japanese Patent Application No. 2021-513428, and an English Translation of the Office Action. (20 pages).

Office Action issued on Mar. 6, 2024, by the U.S. Patent and Trademark Office in U.S. Appl. No. 18/451,888. (40 pages).

Office Action (Notice to File a Response) issued on Jun. 27, 2024, by the Korean Patent Office in corresponding Korean Patent Application No. 10-2021-7010531, and an English Translation of the Office Action. (21 pages).

* cited by examiner

SHEATH FOR A TIP OF A SCANNING DEVICE AND SYSTEM THEREOF

FIELD OF THE INVENTION

This invention generally relates to sheath for a tip of a scanning device. The sheath allows for 3D scanning of intra-human cavities, such as oral-cavities and/or ear-cavities, such that the scanning device does not get contaminated from the outside environment.

BACKGROUND

In the field of 3D scanning, in particular 3D scanning of intra-human cavities, such as intraoral-cavities and/or ear-cavities, contamination of the scanning device is well-known.

Typically, when 3D-scanning for example the teeth of an intraoral cavity, an intraoral scanning device with a tip needs to be put inside the intraoral cavity. This exposes the tip to various bacteria of a first patient. Thus, to scan another patient, the tip must be without the bacteria from the first patient. This problem may be solved by having disposable tips, such that the entire tip is replaced by another disposable tip for each patient. This solution may be associated with a rather high cost, because the tip itself may comprise high-cost elements, such as for example reflective elements and/or electronics. Another solution to the problem may therefore be to sterilize the tip by for example an autoclave in between patients. This solution requires that the tip is configured for autoclaving and is thus also a rather a costly solution.

Disposable sheaths for devices, such as for endoscopes, are known in general. Such disposable sheaths are known to have low cost optical elements, such as optical windows. Such disposable sheaths allow for imaging trough the optical window of for example tissue inside the human body, such that the endoscope does not get contaminated from the outside environment. A sheath for an endoscope is disclosed in US 2017/0290492.

However, 3D scanning is typically very different from endoscopic imaging because a scanner typically requires a light source to project light into the human cavity via the same optical element that is also used for imaging. An endoscope typically also has separate light sources that may reside on the outside of the optical window. Nevertheless, the endoscope as disclosed in US 2017/0290492 has optics for both illumination and imaging, the optics is located in the distal of the endoscope and covered by a sheath.

Because 3D scanning typically requires a light source to project light into the human cavity via the same optical element that is also used for imaging, 3D scanning devices may be very sensitive to any object within the path of the light. If the path of the light is obstructed, even by a transparent surface, the scanning device may experience internal reflections of the light being emitted by the light source inside the scanning device. Internal reflection may affect the imaging during scanning and appear on acquired images as one or more oversaturated bright spot(s) resulting in reduced 3D data quality. One solution to avoid internal reflection may be by using anti-reflective coating. Such coating may also be associated with high cost.

Further, because 3D intraoral scanning typically requires a light source to project light into the human cavity via the same optical element that is also used for imaging and is required to image translucent objects, such as teeth, 3D scanning devices may rely on a specific polarization. Changing the polarization may have severe effect on the image acquisition and model building of a 3D model. Polarization is typically not an issue when using endoscopes because only 2D images are of interest. Further, endoscopes typically image all reflections, and not only for example specular reflections from teeth in an intraoral cavity. A 3D intraoral scanner therefore has more requirements to the optics than is required in a 2D imaging endoscope. One solution to avoid changing the polarization of a 3D scanning device is to not insert an optical element in the path of the intraoral scanning device. However, such a solution may allow for contamination of the intraoral scanning device.

There is thus a need for a low-cost solution to provide sheath for an intraoral scanning tip, at least such that polarization is not altered during scanning and at the same time without contaminating the scanning device.

SUMMARY

The present invention provides in a first aspect a sheath for a scanning tip, where polarization is not substantially altered during scanning.

The present invention provides in a first aspect a sheath configured for being replaceably mounted to at least a part of a tip of an intraoral scanning device, thereby being configured to be used in combination with the intraoral scanning device to scan an intraoral cavity.

The sheath comprises a hollow body comprising a distal sheath-end, a proximal sheath-end, and a sheath-side wall located between the distal sheath-end and the proximal sheath-end, wherein the proximal sheath-end forms a sheath-opening that is dimensioned with respect to at least the part of the tip.

Further, the sheath comprises an optical window mounted to or located in the sheath-side wall near the distal sheath-end such that when the sheath is replaceably mounted to at least the part of the tip via the sheath-opening, the optical window covers at least a part of an optical aperture of the tip.

The optical window is made of a material configured for not substantially altering the polarization of the light that exits and enters the intraoral scanning device through the optical aperture of the tip and through the optical window to and from the intraoral cavity. Thereby, the optical window ensures that the scanning device provides substantially the same scan of the intraoral cavity regardless of the sheath being replaceably mounted to at least the part of tip or not.

In a most preferred embodiment of the first aspect, the optical window has a thickness of more than 400 microns. Accordingly, in most embodiments, the optical window is non-flexible, meaning that the optical window may not, when mounted to or located in the sheath-side wall, bend or similarly deform, at least not easily. However, it is understood that the optical material may be made of a material that is defined to flexible under certain circumstances. For example, if high pressure is applied to an optical window with a thickness of more than 400 microns, then the window may under such circumstance bend or similarly deform.

The present invention, as provided by the first aspect, allows for 3D intraoral scanning with a 3D intraoral scanning device comprising an internal light source that project lights and acquires images through the same optical element, such that no internal reflections are acquired during scanning and/or without altering the polarization during scanning and at the same time such that scanning device does not get contaminated from the outside environment.

Contamination is avoided because the optical window may also be sealed and provides thereby no entrance into the hollow body. The optical window is according to the invention located on or mounted to the sheath-side wall, whereby the scanning device is able to scan to a side, rather than scanning in a forward direction.

Further, the proximal sheath-end of the hollow body may comprise a closed surface such that contamination from the outside is impossible through the proximal sheath-end. Even further, the sheath, i.e. the hollow body may be able to be replaceably fit around at least a part the tip of the scanning device, thereby reducing contamination even further. The hollow body may in some embodiment also able to replaceably fit around a part of the scanning device, and in some embodiments, the entire scanning device. This provides that contamination to the intraoral scanning device is also avoided. Particularly, by having the hollow body covering both the tip and part of the intraoral scanning device, contamination to the part between the intraoral scanning device and the tip is avoided.

The sheath according to the present invention is in most embodiments configured for being disposable and configured to be single-used. Accordingly, the sheath may be made of environmentally friendly materials.

The present invention provides in a second aspect a system of an intraoral scanning device, comprising: a tip of an intraoral scanning device comprising an optical aperture; and a sheath configured for being replaceably mounted to at least a part of the tip of the intraoral scanning device, thereby being configured to be used in combination with the scanning device to scan an oral cavity.

The sheath comprises: a hollow body comprising, a distal sheath-end, a proximal sheath-end, and a sheath-side wall located between the distal sheath-end and the proximal sheath-end, wherein the proximal sheath-end forms a sheath-opening that is dimensioned with respect to at least a part of the tip.

Further, the sheath comprises an optical window mounted to or located in the sheath-side wall near the distal sheath-end such that when the sheath is replaceably mounted to at least the part of the tip via the sheath-opening, the optical window covers at least a part of an optical aperture of the tip.

The optical window is made of a material configured for not substantially altering the polarization of the light that exits and enters the intraoral scanning device trough the optical aperture of the tip and through the optical window to and from the intraoral cavity. Thereby the optical window ensures that the scanning device provides substantially the same scan of the intraoral cavity regardless of the sheath being replaceably mounted to at least the part of the tip or not. In a most preferred embodiment of the second aspect, the optical window has a thickness of more than 400 microns.

The inventors of the present invention have realized that an optimal thickness of the optical window is more than 400 microns because, when more than this, the optical window is able to cover the field-of-view that is typically used in intraoral scanning without being deformed during intraoral scanning. If the optical window would be less than 400 microns, the optical window could easily bend, and this could introduce internal reflections by the optical window that could compromise the imaging quality of the intraoral scanning device. In some cases, when much less than 400 microns, the optical window could even tend to ripple, which severely could compromise the imaging quality of the intraoral scanning device. Accordingly, the inventors found the thickness of more than 400 microns to be an optimal thickness to provide optimal imaging in an intraoral scanning device. Further, the inventors have realized that the thickness of more than 400 microns may also ensure that the optical window does not break during scanning. For example, in intraoral scanning with the intraoral scanning device, the scanning tip very often comes into contact with teeth, sometimes even sharp teeth, and if there is a window of less than 400 microns, such window could easily break and splinter into the mouth of a patient. In some cases, when much less than 400 microns, the optical window could even tend to puncture or crack. Such scenarios must be avoided and therefore a solution to the scenario may be to provide the optical window with a thickness of more than 400 microns. However, as describe before, in intraoral scanning, introducing an optical window with a thickness of more than 400 microns may for many materials change the polarization of the emitted light, whereby this may have severe effect on the image acquisition, but most importantly the model-building of a 3D model. Accordingly, the present invention requires that the optical window is made of a material configured for not substantially altering the polarization. This is also the case when introducing a window with a thickness of more than 400 microns. Where many materials with a thickness of less than 400 microns may not alter the polarization, many materials with of a thickness of more than 400 microns may indeed alter the polarization. Therefore, when introducing the window with a thickness of more than 400 microns, the material must be carefully selected such that it does not substantially alter the polarization and/or introduces internal reflection. When introducing the window with a thickness of more than 400 microns, one therefore must carefully consider both the effect of the selected material and the thickness of the optical window. Various of such considerations and embodiment of the invention are presented in the following.

BRIEF DESCRIPTION OF THE DRAWINGS

The above and/or additional objects, features and advantages of the present disclosure, will be further described by the following illustrative and non-limiting detailed description of embodiments of the present disclosure, with reference to the appended drawing(s), wherein.

DETAILED DESCRIPTION

Optical Window

Figure 1:
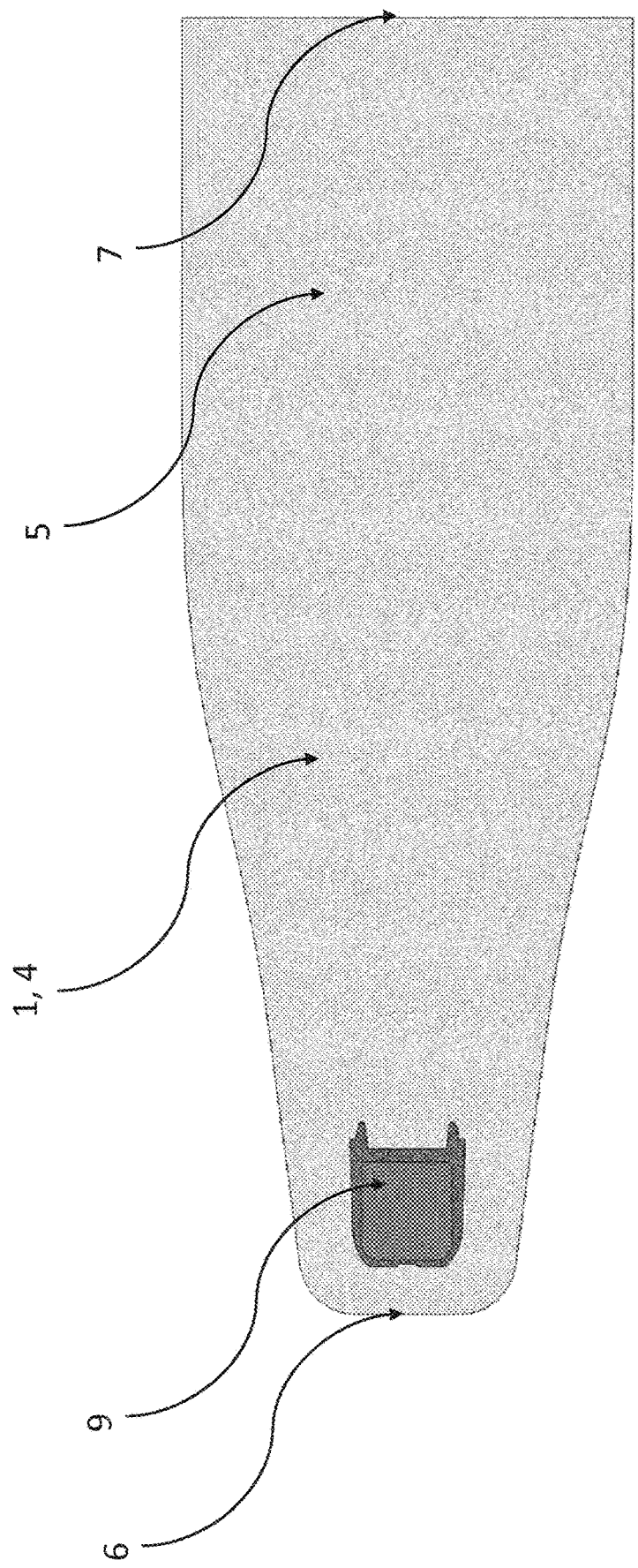
FIG. 1 shows an example of a flexible sheath.

In one embodiment, the thickness of the optical window is more than 600 microns or more than 800 microns, or more than 1000 microns. The inventors have found that when introducing these thicknesses, the optical window becomes more stable and is less prone to break, particularly when being used to intraorally scan the intraoral cavity with an intraoral scanner having thereon the sheath of the present invention.

Introducing an optical window with a substantial thickness in an intraoral scanning device, particularly on the tip of the intraoral scanning device, of course also makes the tip thicker. Accordingly, in another embodiment, for example to not introduce too much discomfort of the patient during scanning, the thickness may be between 400 microns and 5000 microns. In preferred embodiments, the thickness may be between 800 microns and 2000 microns.

In most preferred embodiments, as have already been described, the thickness is selected to not substantially deform the optical window during the scan of the oral cavity. Examples of scenarios with deformation and examples of the thicknesses that provide the solution to avoid the scenarios have been described above.

Also as has already been described, in other embodiments, the material of the optical window has a hardness that is selected to withstand the impact of teeth in the intraoral cavity.

In one embodiment, the optical window is made of a material, wherein the material is configured for not substantially altering the polarization of the light that exits and enters via the optical window. For example, the material of the optical window may be selected to be one or more polymer(s). A polymer may combine the optical characteristics of glass with the design-freedom of a molded or extruded plastic. Further, a polymer may be advantageous because inorganic nanocrystals can be added to the polymer(s). A polymer may be defined to flexible, at least in free-form, and at least when the polymer(s) form(s) a window that is less than 400 microns thick and more than 10 square mm. Accordingly, a polymer may be said to be non-flexible when at least the thickness is more than 400 microns. More generally, when an optical window is located to or mounted in the sheath, the optical window typically is in a state, where it can be defined to be non-flexible.

In another example, the optical window may be made of glass and/or quarts.

In general, the optical window may have some degree of birefringence, whereby the optical window is within the context of being configured such that it not substantially alters the polarization of the light. For example, the optical refractive index (known as $n_o$ and $n_e$) along the two optical directions inside the optical window may differ by up to 15% to not substantially alter the polarization of the light. By choosing such a window, 3D scanning may be substantially unaffected by the window. In some embodiments, the optical refractive index along the two optical directions inside the window may differ between 0.1% and 14%, such as between 0.4% and 10%, such as between 1% and 5%. In other embodiments, the optical refractive index along the two optical directions may be less than 15%, such as less than 10%, such as less than 6%, such as less than 3%, or such as less than 1%.

Birefringence can be quantified in units nm/cm, i.e. optical path length (in nm) over materials thickness (in cm). Optical quality glass is in the range 2-20 nm/cm.

For birefringence to not substantially alter the polarization of the light, the optical window may be defined to have a birefringence of around 2500 nm/cm.

In some embodiments, the optical window may be defined to have a birefringence such as around 100.000 nm/cm or less, such as around 10.000 nm/cm or less, such as around 1.000 nm/cm or less, such as around 100 nm/cm or less, or around 10 nm/cm or less.

In most preferred embodiments, the optical refractive index along the two optical directions differs less than 1%, corresponding to a birefringence of less than 100.000 nm/cm. In this embodiment, scanning can be performed without substantially affecting the polarization.

Examples of one or more polymer(s) exhibiting low birefringence and at the same time also provide(s) high optical clarity, are:
  Poly(methyl methacrylate) (PMMA) (in cast quality it can be made with very low birefringence, in extruded quality the birefringence is higher but still acceptable);
  Cellulose diacetate and/or cellulose triacetate;
  low molecular weight polycarbonate resin (e.g. bisphenol-A polycarbonate), for example produced by a special processing equipment which reduces stress in the optical window to keep birefringence below 20 nm;
  Acrylate polymers with a tetraphenylethane skeleton in the side chain;
  Cyclo Olefin Polymer (COP);
  Polyester Containing Fluorene Side Chain;
  poly(phenylene thioether)s with a fluorene-based cardo structure;
  poly(methyl methacrylate) doped with trans-stilbene as an anisotropic molecule;
  highly fluorinated acrylic macromers and/or monomers containing perfluoroalkyl, perfluorophenyl, and perfluorocyclohexyl pendant groups;
  pullulan esters derivatives (PLEs).

These materials have been found to not substantially alter the polarization of the light.

In a preferred embodiment, the optical window is made of cellulose diacetate. This polymer has several advantages in provides example high transparency and transmittance, it has exceptionally low haze, near zero birefringence, is UV stable, has good tensile strength and elongation, relatively low tear strength, high stiffness, extremely low water permeability, dimensionally stable, light weight, and easy to cut. Furthermore, it can be made as an anti-fog window.

In another preferred embodiment, the material is selected to be a polyester resin composition and a polycarbonate resin composition. This a material has been found to substantially not altering the polarization when used as the optical window on the sheath according to the present invention. Furthermore, this material has been found to be a very good candidate for making the optical window as injection-molded. When this material is injection-molded, the inventors have found that this material does not introduce birefringence, i.e. it does not introduce stress in the material, as many other materials do when they are injection-molded. At the same time, the material has very good optical properties, such as a optimal Abbe number, that makes it an optimal solution for an optical window in a sheath according to the invention, even for color 3D scanning. Finally, in some embodiments, the optical window may be injection-molded, for example with this material, and this also reduces the manufacturing costs in comparison to other manufacturing processes.

In many embodiments, the optical window is glued, or sealed, or welded into the hollow body.

In one embodiment the optical window is mechanically sealed in the hollow body by means of a rubber gasket. In a preferred solution, the rubber gasket is made from the same material as the body In other embodiments, the optical window is an integrated part of the hollow body. For example, both the hollow body and the optical window may be made in one step, this one-piece, as an injection-molded sheath. In this sense, the window may still be said to be located in the hollow body, although there may be no visual difference between the hollow body and the optical window.

In one embodiment, the optical window covers the optical aperture of the tip such that the field-of-view in the intra-oral cavity is maintained.

In a related embodiment, the optical window is larger than 10 mm by 10 mm. Such a window is typically preferred in intraoral scanning as this may provide a preferred field-of-view in the intraoral cavity.

Polarization may be affected by the structure of the surface, and thus in most embodiments, the optical window is planar and/or comprises a planar surface. This may contribute to not altering the polarization of the light. In some embodiments of the invention, the optical window is a non-flexible optical window mounted in the body. However, a non-flexible window may in some embodiments be realized by suspending a flexible window inside a non-flexible frame, for example a frame made of stainless steel or another rigid material.

In another embodiment, a non-flexible optical window is made from a thin semi-flexible polymer which is shaped in a way to provide a framework of high stiffness and rigid properties of the part of the optical window.

In a second embodiment, at least a part of the optical window is dimensioned to mechanically couple to a coupling unit on the tip. This embodiment allows the surface normal to deviate from the optical axis, whereby internal reflections of the light that exits via the tip is guided away from the optical axis. Further, this embodiment allows the window to be means for coupling to the tip. Thus, an advantage of this embodiment is that the optical window provides the mounting of the sheath to the tip.

In a preferred embodiment, the optical window comprises a hydrophilic surface. An advantage of a hydrophilic surface is the avoidance of water droplet formation on the window, for example due to fogging in a humid environment, for example from the breath of a patient. The hydrophilic surface may be realized by a hydrophilic coating or as an intrinsic property of the optical window. In one embodiment, the optical window is treated with an anti-fog agent, for example in the form a coating. By having a hydrophilic surface, water forms a thin film on the surface, and thereby avoids the formation of water droplets. The thin film does not spread the light in the same manner as water droplets would do. Accordingly, an optical window comprising a hydrophilic surface is advantageous in 3D scanning because the scanning can be performed without altering the light coming in and out of the scanner.

In some embodiments, the optical window is configured to absorb light in the near infrared domain and/or in the lower visible domain. An advantage of such a configuration is that that window may be heating via optical means. This may be an alternative to having a hydrophilic window as heating can also prevent water droplets forming on the window.

Body of the Sheath

In one embodiment, the hollow body is in the form of a tubular member.

In another embodiment, the hollow body is flexible. The advantage of this embodiment is that the optical window may adapt to an angled surface of the tip because the flexible hollow body provides for such an adaption. For example, the optical window may be mounted on the flexible body such that when the optical window is non-flexible, the optical window is allowed to be angled by pulling the flexible hollow body, the flexible hollow body may be elastic or non-elastic to allow for such angling.

In an alternative embodiment, the hollow body is non-flexible, i.e. rigid. A rigid hollow body may be obtained by injection-molding. A non-flexible hollow body has the advantage of being handled more easily especially when the hollow body needs to be put onto the tip.

In yet another embodiment, the hollow body is semi-flexible, such that the body may self-support its own shape, but at the same time flexible enough to adapt to the scanner tip and/or part of the scanning device, for example to ensure a tight fit. Such a semi-flexible structure can, for example, be obtained by blow-molding a polymer material.

In a second embodiment the hollow body is made of one or more polymer(s). In some embodiments, the hollow body is made of the same material as the optical window.

In an alternative embodiment, as described for the optical window, the hollow body is made of a polyester resin composition and a polycarbonate resin composition.

In most embodiment, the sheath is made of one or more material(s) that is/are adapted to be inserted into the intraoral cavity.

In most preferred embodiments, the sheath is made of one or more material(s) that is/are adapted to be a single-use sheath.

Tip and Coupling Unit

As previously described for the second aspect of the invention, the system comprises a sheath and a tip.

In some embodiments, the sheath is the sheath according to first aspect as described above.

In one embodiment, the tip comprises a tip-body configured to allow light to exit and enter the intraoral scanning device to and from an intraoral cavity trough the aperture, wherein the tip-body comprises a proximal tip-end, a distal tip-end, and a tip-side wall located between the proximal tip-end and the distal tip-end, wherein the proximal tip-end forms an opening that is mounted to or located in the intraoral scanning device, and wherein the aperture is located in the tip-side wall near the distal tip-end. Such a tip may be configured for scanning through the tip side wall, which makes scanning of intraoral cavities easier than scanning though a distal tip-end.

In most embodiment, where for example the intraoral scanning is through the tip-side wall, the tip comprises a mirror inside the tip-body, wherein the mirror is configured to direct the light from the intraoral scanning device and to the intraoral cavity via the optical aperture and back the same way into the intraoral scanning device.

In one embodiment, the optical aperture of the tip allows for mechanical access into the tip-body such that when the sheath is replaceably mounted to at least the part the tip via the sheath-opening, then the sheath blocks the mechanical access. This prevents contamination of the inside of the tip.

In some embodiments, the tip is configured for being replaceably mounted to the intraoral scanning device. By having both a replaceably tip and a replaceably sheath, contamination of the scanning device is reduced to a minimum. First of all, it allows the user to disinfect both the tip and the sheath and/or to disinfect the tip and to use a new disposable sheath for the tip. Secondly, the scanning device itself need not to be sterilized, such as for example in an autoclave.

Accordingly, the invention provides with this embodiment for effectively avoiding contamination of the scanning device.

In one embodiment, the tip comprises an optical axis, where a mirror is located on the optical axis such that the optical axis is redirected inside the tip. This may allow for the scanning device to scan to the side rather than in a forward direction.

In one embodiment, the tip comprises a coupling unit that is dimensioned to mechanically couple at least a part of the optical window to the tip. This embodiment allows the surface normal to deviate from the optical axis, whereby internal reflections of the light that exits via the tip is guided away from the optical axis. Further, this embodiment allows the window to be means for coupling to the tip. Thus, an advantage of this embodiment is that the optical window provides the mounting of the sheath to the tip.

In a second embodiment, the coupling unit is configured such that when the optical window is mounted to the tip, the surface normal of the optical window deviates from the optical axis of more than 5 degrees, such as more than 10 degrees, such as between 10 and 30 degrees, such as between 10 and 20 degrees, such as between 10 and 15 degrees, such as around 12 degrees, such as around 11.5 degrees and/or such as around 12.5 degrees. This allows for a reflected spot to be directed out of the sensor area.

By having a surface normal that deviates from the optical axis, the internally reflected light is not guided directly back on the optical axis as the case would be if the surface normal would be parallel to the optical axis. Thus, the internally reflected light is not guided towards an imaging sensor in the scanning device and avoids the use of anti-reflective coating. Instead, by the above embodiment, internally reflected light is guided out of the sensor area by having the surface normal of the optical window angled relative to the optical axis. Thus, the above embodiment provides a low-cost solution to a sheath for a scanning device, where the objective is to avoid internal reflections. Angling of the surface normal of the optical window may be achieved in many ways. For example, if the sheath comprises a non-flexible body, the non-flexible body may have an angled surface, whereon the optical window is mounted. Alternatively, if the sheath comprises a flexible body, the tip may have an angled surface, whereon the optical window is mounted. In this latter example, the optical window may adapt to the angled surface of the tip because the flexible body provides for such an adaption. For example, the optical window may be mounted on the flexible body such that the optical window is allowed to be angled by pulling the flexible body. The flexible body may be elastic or non-elastic to allow for such angling.

In another embodiment, the coupling unit is a slit or a groove, wherein the slit or groove has a height larger than a thickness of the optical window, and/or wherein the slit or groove has a length and/or width that is less than the length and/or width of the optical window, such as a half of the optical window, or such as a third of the optical window, or such as a tenth of the optical window. The specified thickness allows for the optical window to fit into the slit and the specified length and/or width allows for saving material, such that the sheath can be manufactured with low cost.

In a preferred embodiment, the coupling unit is located around a part of the aperture such that the optical window is able to be coupled on top of the aperture. This allows for light to exit and enter the optical axis via the aperture and the optical window, especially such that the aperture gets closed, whereby contamination is avoided.

Intraoral Scanner

In one embodiment of the second aspect, the system further comprises the intraoral scanner. The intraoral scanner is configured for forming a 3D model of the intraoral objects such as teeth and gingiva. Typically, the intraoral scanner comprises a light source to emit light, for example to project a pattern onto the intraoral objects, whereby this pattern is used by imaging of the intraoral scanning device to form the 3D model.

In one embodiment, the intraoral scanner is configured to emit the light as linearly polarized light.

In another embodiment, the intraoral scanner is configured to emit the light as circularly polarized light. In this embodiment, when the circularly polarized light is specularly reflected from the intraoral objects, the helicity of the polarization changes, for example from right hand circular polarized to left hand circular polarized. Accordingly, circular polarized light is received at the optical window of the sheath, and to image the specular reflections, the scanner is configured, for example by comprising a quarter wave retarder, to only allow light with circular polarized light to pass into the imaging device. In such a scanner, it is of uttermost critical importance that optical window of the sheath according to the invention does not substantially alter the polarization—if it did, the result of the 3D model would be very dramatically changed and would possibly not be precise enough for use in relation with a tooth restoration or other important operations that are governed by a 3D model.

Example 1—A Flexible Sheath as Shown from a Top-View

FIG. 1 shows an example of the sheath (1) according to the invention from a top-view.

FIG. 1 shows a sheath (1) for a tip (2) of a scanning device (3), comprising: a body (4) in the form of a tubular member (5) comprising a distal end (6) and a proximal end (7). The proximal end (7) comprises an opening (8) that is dimensioned with respect to at least the tip (2) of the scanning device (3), such that the tubular member (5) is able to be replaceably mounted to at least a part of the tip (2) of the scanning device (3).

The body (4) comprises a non-flexible optical window (9) mounted in the body between the distal end (6) and the proximal end (7) of the body, such that the optical window (9) allows for light to exit and to enter the scanning device (3) via an optical axis (10) inside the tip (2). The optical window (9) is mounted in the body (4) such that when the tubular member (5) is replaceably fit around at least the tip (2) of the scanning device (3), the optical window (9) comprises a surface normal (11) that deviates from the optical axis (10), whereby internal reflections of the light that exits via the tip (2) is guided away from the optical axis (10). As cannot be seen from the figure, the optical window (9) is made of a material, wherein the material is configured for not substantially altering the polarization of the light that exits and enters via the optical window (9).

The optical window (9) comprises a planar surface and the optical window (9) is dimensioned to mechanically couple to a coupling unit (13) on the tip (2).

In this example, the body (4) is made of plastic and is flexible. In other words, the body (4) is a plastic bag. The body is shown lying flat. In other words, only the top surface of the body (4) is shown.

The optical window (9) may be fastened to a stamped cutout, for example the optical window may be a hard polymer window that is glued and/or welded to inside of the plastic bag.

Alternatively, the optical window (9) may be part of the flexible plastic body and suspended in a frame to ensure flatness of window, for example wherein the frame is glued to the inside of the plastic body.

The plastic bag as here shown is cheap to produce since production can be fully automated. Further, the flatness of the optical window (9) can be fully ensured.

A great advantage of a flexible body is that it has very low volume when packed, especially because the body (4) is flat when not attached to the tip (2) of the scanning device (3).

Example 2—An Optical Window as Shown Un-Mounted

Figure 2:
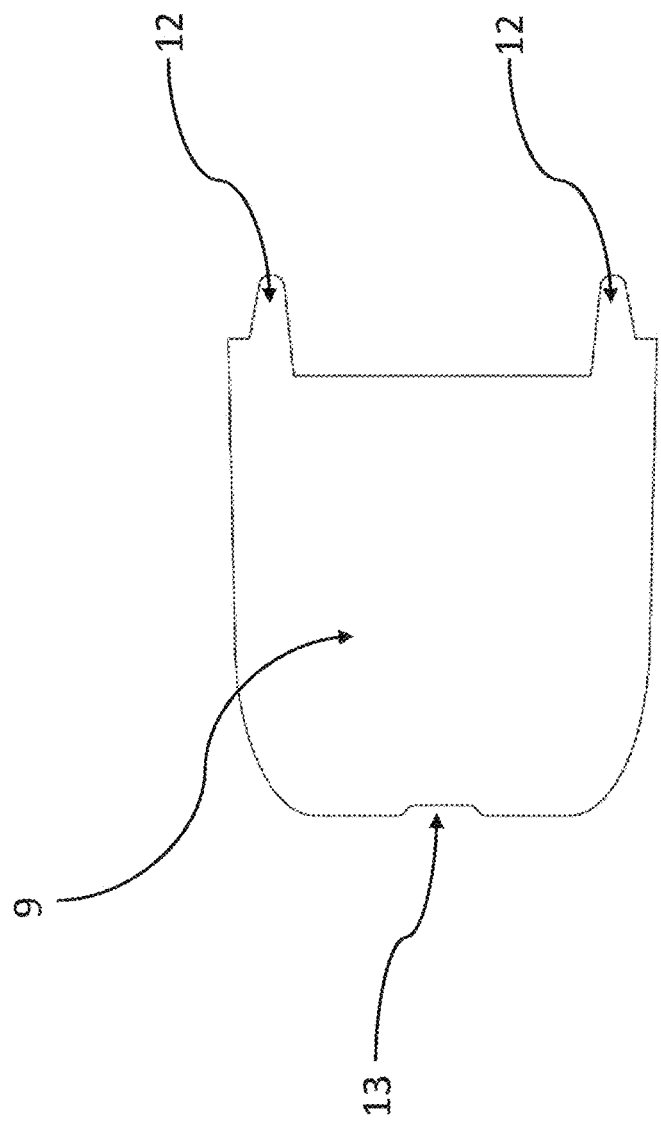
FIG. 2 shows an example of an optical window.

FIG. 2 shows an example of the optical window according to the invention.

The optical window (9) is here shown un-mounted from the body (4).

However, the optical window is formed such that when the body (4) is replaceably fit around at least the tip (2) of the scanning device (3), the optical window (9) comprises a surface normal (11) that deviates from the optical axis (10), whereby internal reflections of the light that exits via the tip (2) is guided away from the optical axis (10). In other words, the optical window is configured such that when the body (4) is replaceably fit around at least the tip (2) of the scanning device (3), the optical window (9) comprises a surface normal (11) that deviates from the optical axis (10), whereby internal reflections of the light that exits via the tip (2) is guided away from the optical axis (10).

The configuration of the surface normal in relation to the optical axis is ensured by the optical window comprising guide members (12). These guide members (12) can for example be used to guide the optical window (9) into a position on the tip (2), such that the optical window (9) is placed at the tip (2) and at an angle, a, relative to the optical axis (10). The optical window also has a part (13) configured such that the optical window is able to lock in the tip (2), here in the form of an indent, configured to lock into a locking mechanism (17) for the optical window (9), shown in FIG. 3.

Example 3—A Tip of a Scanning Device as Shown from the Outside

Figure 3:
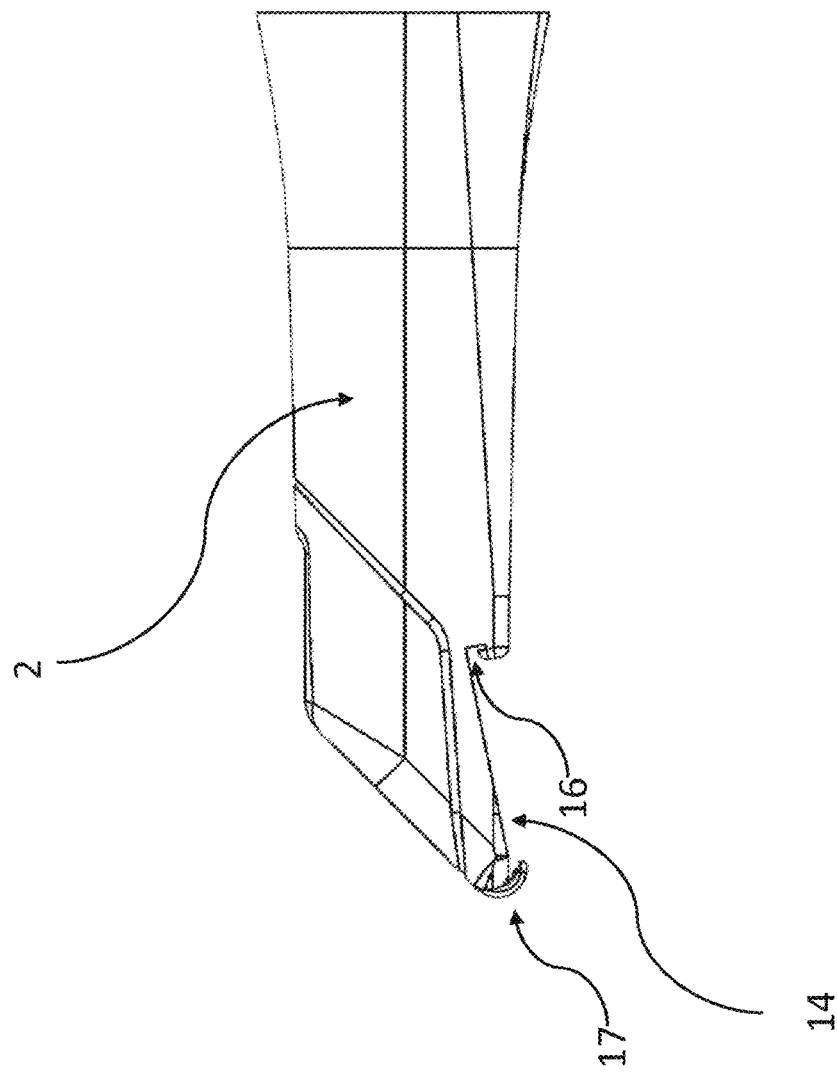
FIG. 3 shows an example of a tip of a scanning device

FIG. 3 shows an example of a tip (2) for the scanning device (3) according to the second aspect of the invention, shown from the outside.

FIG. 3 shows a tip (2) for the scanning device (3), wherein the tip is replaceably mountable on the scanning device (3), the tip comprising an aperture (14) on an optical axis such that light is allowed to exit and to enter the scanning device via the optical axis (10).

The tip (2) comprises a mirror (15) located on the optical axis (10) such that the optical axis (10) is redirected inside the tip (2). The mirror (15) and optical axis (10) cannot be seen in this figure, since only the outside is shown. However, this can be seen in the next figure, FIG. 4.

The tip (2) comprises a coupling unit (16) that is dimensioned to mechanically couple at least a part of the optical window (9) to the tip. The coupling unit (16) is configured such that when the optical window (9) is mounted to the tip (2), the surface normal (11) of the optical window (9) deviates from the optical axis (10) of around 11.5 degrees. The surface normal (11) of the optical window (9) deviates from the optical axis by and angle referred to as α. This is clearly shown in FIG. 4.

As can be seen in FIG. 3, the coupling unit (16) is a groove, wherein the groove has a height larger than a thickness of the optical window (9). The groove has a length and/or width that is less than the length and/or width of the optical window, here around a tenth of the optical window. As can also be seen in FIG. 3, the coupling unit (16) is located around a part of the aperture (14) such that the optical window (9) is able to be coupled on top of the aperture (14), i.e. on the outside of the aperture (14).

The tip (2) comprises a locking mechanism (17) for the optical window (9), in this example a snap-lock, whereon the part (13) of the optical window (9) matches.

The tip (2) may be an injection-molded tip.

Example 4—A Tip of a Scanning Device as Shown from the Inside

Figure 4:
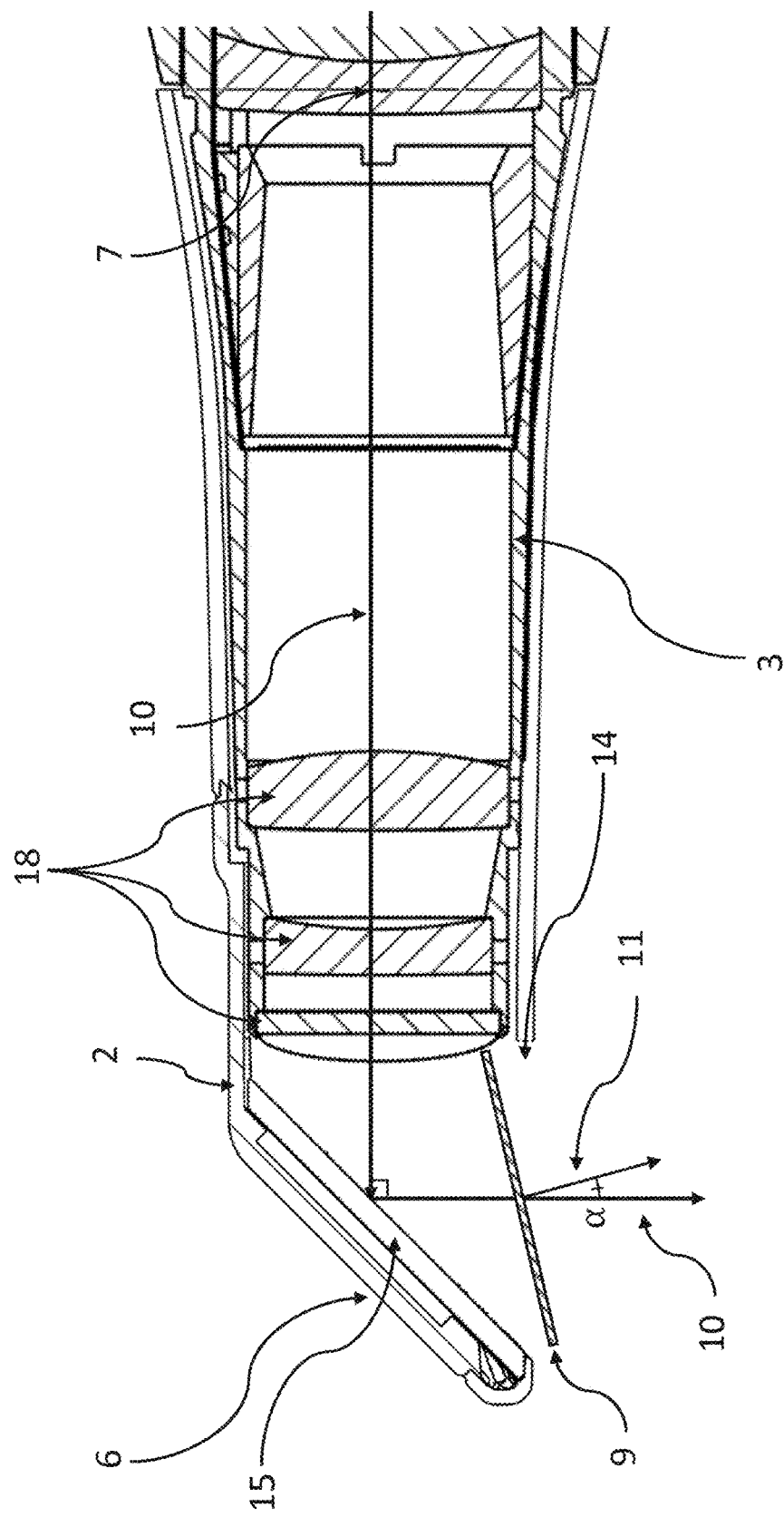
FIG. 4 shows an example of a tip of a scanning device

FIG. 4 shows an example of a tip (2) for the scanning device (3) according to the second aspect of the invention, shown from the inside. Parts of the sheath are also shown in relation to parts of the tip (2)—for seeing these parts in relation to each other. FIG. 4 shows a tip (2) for the scanning device (3), wherein the tip is replaceably mountable on the scanning device (3), the tip comprising an aperture (14) on an optical axis (10) such that light is allowed to exit and to enter the scanning device via the optical axis (10). Optical elements (18) are shown to reside inside the scanning device (3).

The tip (2) comprises a mirror (15) located on the optical axis (10) such that the optical axis (10) is redirected inside the tip (2). The mirror (15) and optical axis (10) are clearly seen here in FIG. 4. As can be seen from this figure, the mirror is tilted 45 degrees relative to the optical axis (10).

Accordingly, the optical axis is directed such that the optical axis comprises two optical axes that are perpendicular to each other, however the two optical axes defining the optical system of the scanning device. However, in some embodiments, the mirror is tilted less or more than 45 degrees relative to the optical axis (10), for example such that the light exits the aperture at an angle which is different from being perpendicular to the optical axis along the body, i.e. the optical axis going from the proximal end (7) to the distal end (6).

The tip (2) comprises a coupling unit (16) that is dimensioned to mechanically couple at least a part of the optical window (9) to the tip. The coupling unit (16) is configured such that when the optical window (9) is mounted to the tip (2), the surface normal (11) of the optical window (9) deviates from the optical axis (10) of around 11.5 degrees. The surface normal (11) of the optical window (9) deviates from the optical axis by and angle referred to as a. This is clearly shown in FIG. 4.

If the mirror would have been placed at an orientation with less or more than 45 degrees relative to the optical axis (10), then the optical window can be placed flush with the tip (2), i.e. parallel to the optical axis (10) along the body (4), i.e. the optical axis (10) going from the proximal end to the distal end. In this manner, the surface normal (11) of the optical window (9) would also deviate from the optical axis (10).

Figure 5:
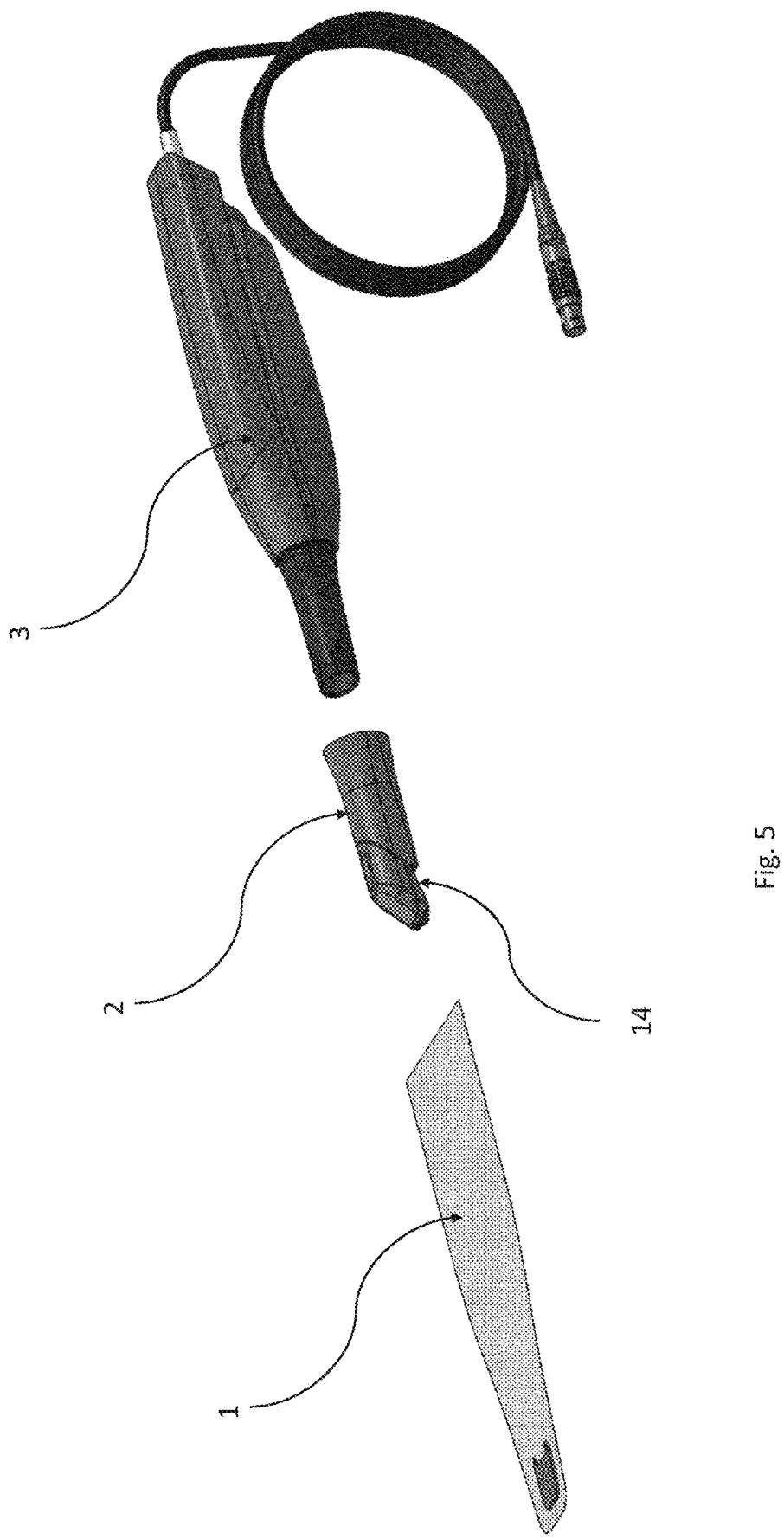
FIG. 5 shows an example of a system comprising a sheath for a tip of a scanning device

Example 5—A System Comprising a Sheath for a Tip of an Intraoral Scanning Device, Shown as Un-Mounted FIG. 5 shows a system of an intraoral scanning device (3), comprising: the sheath (1) as shown in FIG. 1, a tip (2) for the intraoral scanning device (3), wherein the tip (2) is replaceably mountable on the intraoral scanning device (3). The tip (2) comprises an aperture (14) on an optical axis such that light is allowed to exit and to enter the intraoral scanning device (3) via the optical axis (10). In FIG. 5, the sheath (1), the tip (2) and the scanning device (3) are shown as unmounted from each other.

Figure 6:
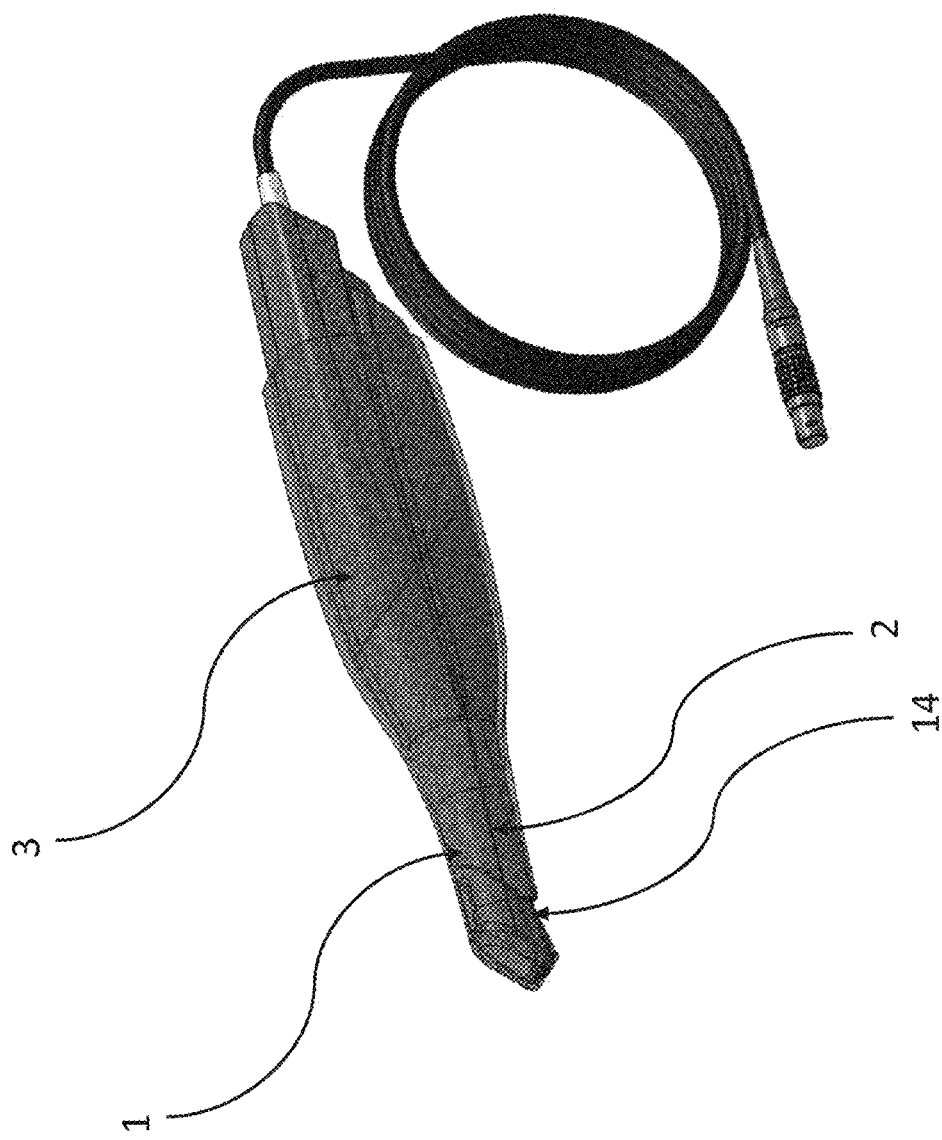
FIG. 6 shows an example of a system comprising a sheath for a tip of a scanning device.

Example 6—A System Comprising a Sheath for a Tip of a Scanning Device, Shown as Mounted FIG. 6 shows a system of an intraoral scanning device (3), comprising: the sheath (1) as shown in FIG. 1, a tip (2) for the intraoral scanning device (3), wherein the tip (2) is replaceably mounted on the scanning device (3). The tip (2) comprises an aperture (14) on an optical axis such that light is allowed to exit and to enter the scanning device (3) via the optical axis (10). In FIG. 6, the sheath (1), the tip (2) and the scanning device (3) are shown as mounted to each other.

Example 7—A Semi-Flexible Sheath as Shown from a Perspective View

Figure 7:
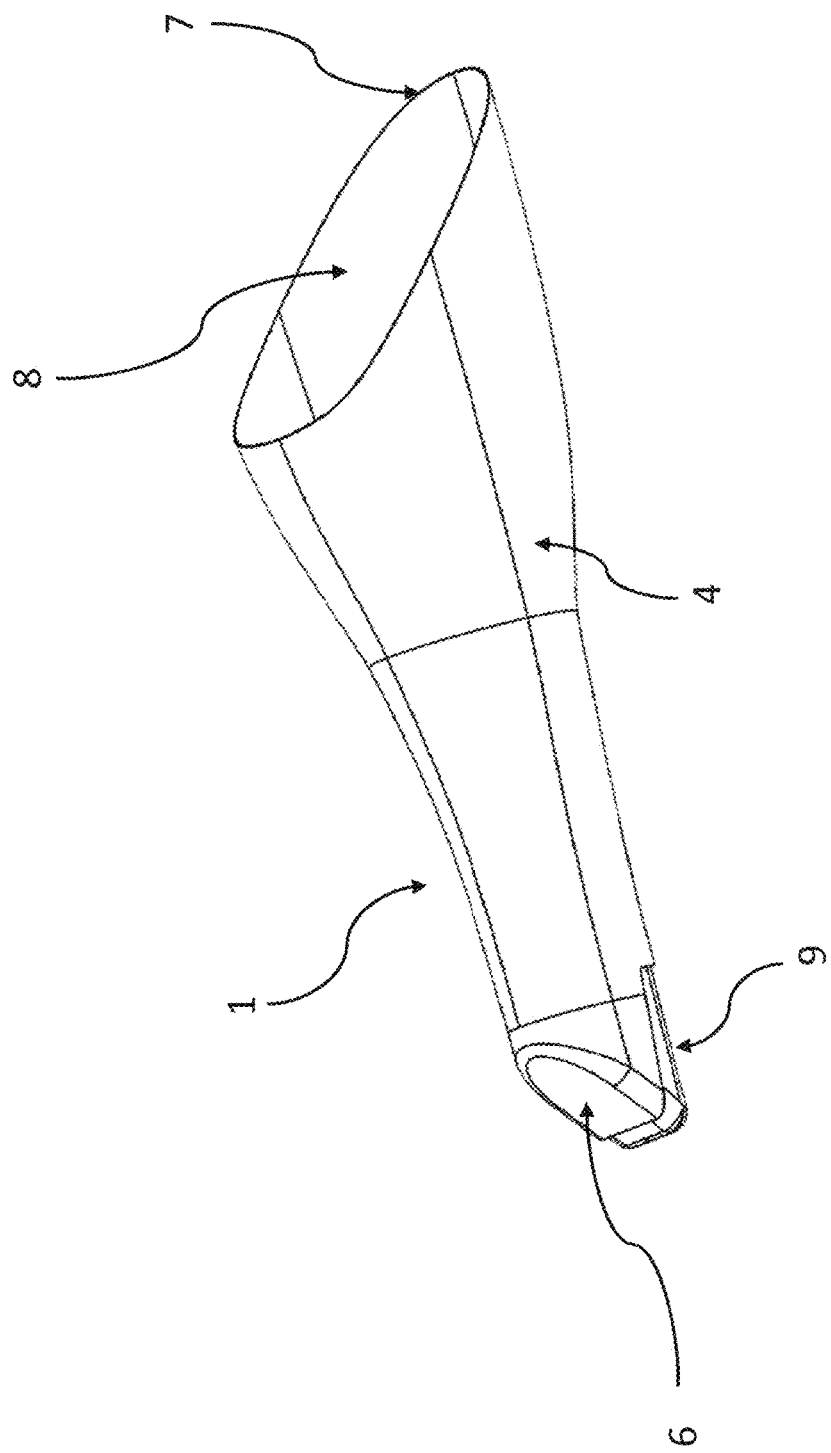
FIG. 7 shows an example of a semi-flexible sheath

FIG. 7 shows another example of the sheath (1) according to the invention.

FIG. 7 shows a semi-flexible sheath (1) for a tip (2) of a scanning device (3), comprising: a semi-flexible body (4) comprising a distal end (6) and a proximal end (7). The proximal end (7) comprises an opening (8) that is dimensioned with respect to at least the tip (2) of the scanning device (3), such that the body (4) is able to replaceably fit around at least a part of the tip (2) of the scanning device (3).

The body (4) comprises a non-flexible optical window (9) mounted in the body between the distal end (6) and the proximal end (7) of the body, such that the optical window (9) allows for light to exit and to enter the scanning device (3) via an optical axis (10) inside the tip (2). The optical window (9) is mounted in tip (3) such that the optical window (9) comprises a surface normal (11) that deviates from the optical axis (10), whereby internal reflections of the light that exits via the tip (2) is guided away from the optical axis (10).

The optical window (9) is located in the body. The sheath (1) is dimensioned to fit around at least part of the tip (2) of the scanning device (3). In the shown example in FIG. 7 the optical window (9) is made from a suitable injection-molded polymer and the body (4) is made from a thin blown molded polymer, whereto the optical window (9) is mounted.

Example 8—An Optical Window as Shown Un-Mounted

Figure 8:
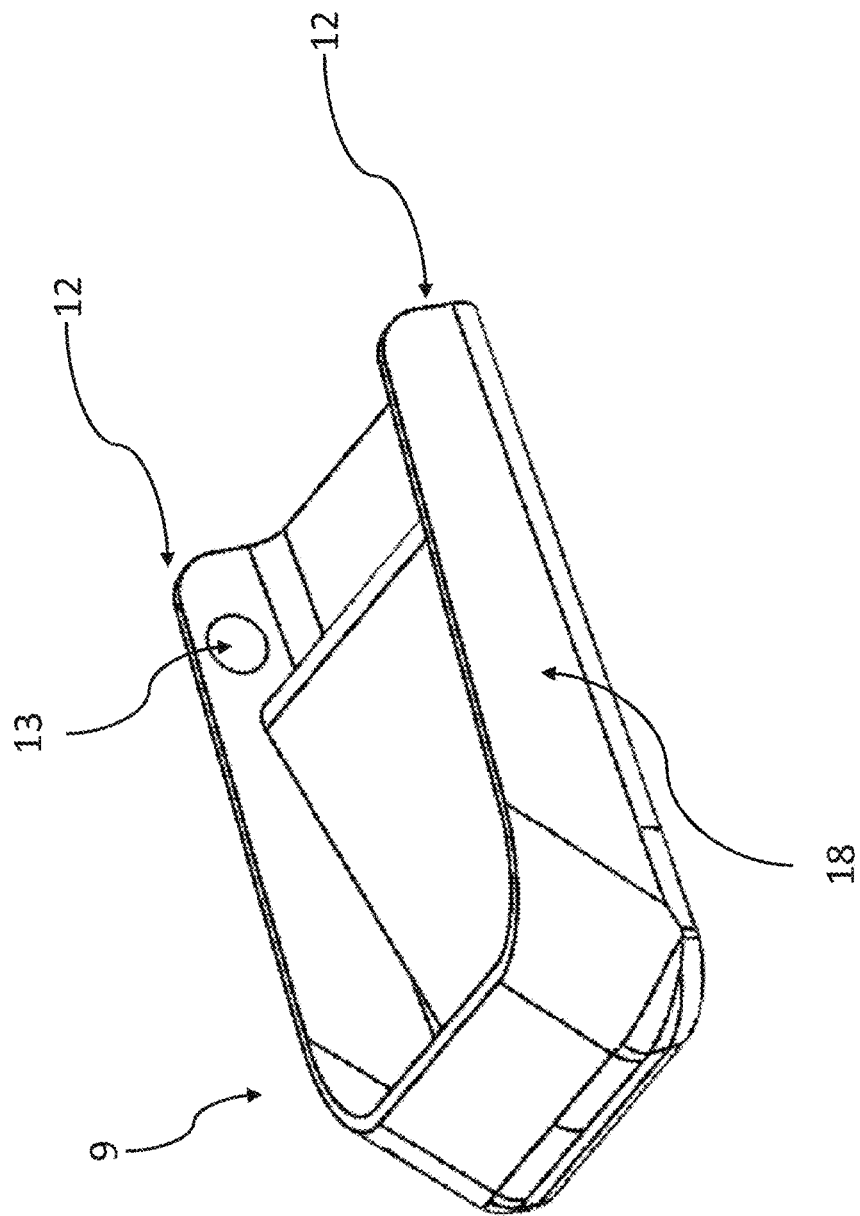
FIG. 8 shows an example of an optical window for a sheath.

FIG. 8 shows another example of the optical window according to the invention.

The optical window (9) is here shown un-mounted from the body (4).

Figure 9:
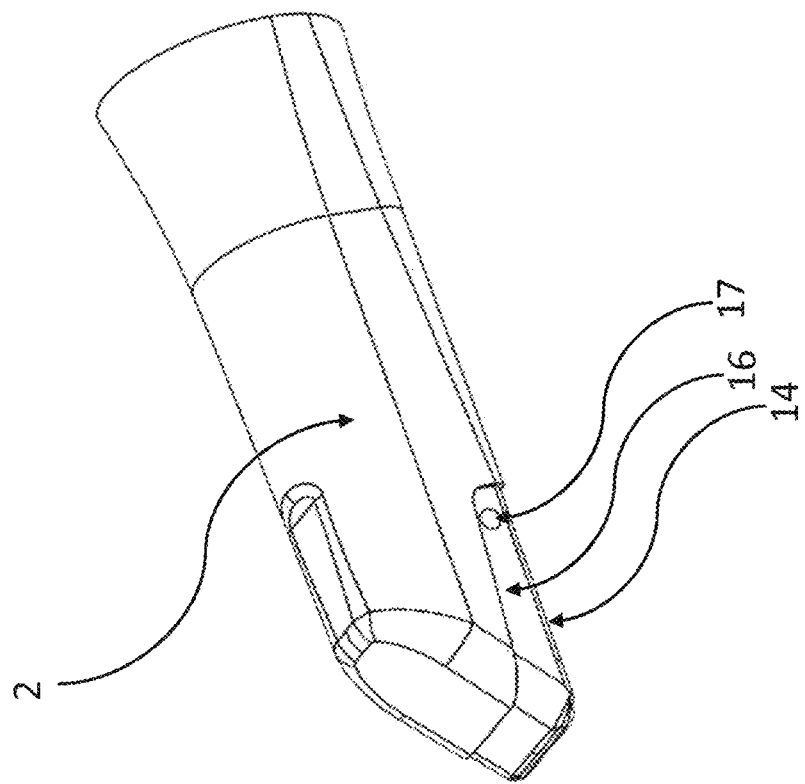
FIG. 9 shows an example of a tip of a scanning device.

However, the optical window is formed such that when mounted to a the tip (2) as shown in FIG. 9 of the scanning device (3), the optical window (9) comprises a surface normal (11) that deviates from the optical axis (10), whereby internal reflections of the light that exits via the tip (2) is guided away from the optical axis (10). In other words, the optical window is configured such that when fit into the tip (2) of the scanning device (3), the optical window (9) comprises a surface normal (11) that deviates from the optical axis (10), whereby internal reflections of the light that exits via the tip (2) is guided away from the optical axis (10).

The configuration of the surface normal in relation to the optical axis is ensured by the rigid frame (18) as part of the optical window (9) comprising guide members (12). In other words, the optical window comprises a rigid frame (18). The guide members (12) can for example be used to guide the optical window (9) into a position on the tip (2), such that the optical window (9) is placed at the tip (2).

The optical window also has a part (13) configured such that the optical window is able to lock in the tip (2), here in the form of a protrusion, configured to lock into a locking mechanism (17) for the optical window (9), shown in FIG. 9.

Example 9—A Tip of a Scanning Device as Shown from the Outside

FIG. 9 shows another example of a tip (2) for the scanning device (3) according to the second aspect of the invention, shown from the outside.

FIG. 8 shows a tip (2) for the scanning device (3), wherein the tip is replaceably mountable on the scanning device (3), the tip comprising an aperture (14) on an optical axis such that light is allowed to exit and to enter the scanning device via the optical axis (10).

The tip (2) comprises a mirror (15) located on the optical axis (10) such that the optical axis (10) is redirected inside the tip (2). The mirror (15) and optical axis (10) cannot be seen in this figure, since only the outside is shown.

As can be seen in FIG. 9, the coupling unit (16) is a groove. As can also be seen in FIG. 9, the coupling unit (16) is located around a part of the aperture (14) such that the optical window (9) is able to be coupled on top of the aperture (14), i.e. on the outside of the aperture (14).

The tip (2) comprises a coupling unit (16) that is dimensioned to mechanically couple the optical window (9) (shown in FIG. 8).

The coupling unit (16) is configured such that when the optical window (9) is mounted in the tip (2), the surface normal (11) of the optical window (9) deviates from the optical axis (10) of around 11.5 degrees. The surface normal (11) of the optical window (9) deviates from the optical axis by and angle referred to as α.

The tip (2) comprises a locking mechanism (17) for the optical window (9) shown in FIG. 8. In this example, a snap-lock in the form of an intrusion, matching the protrusion (13) of the optical window.

The tip (2) may be an injection-molded tip.

Figure 10:
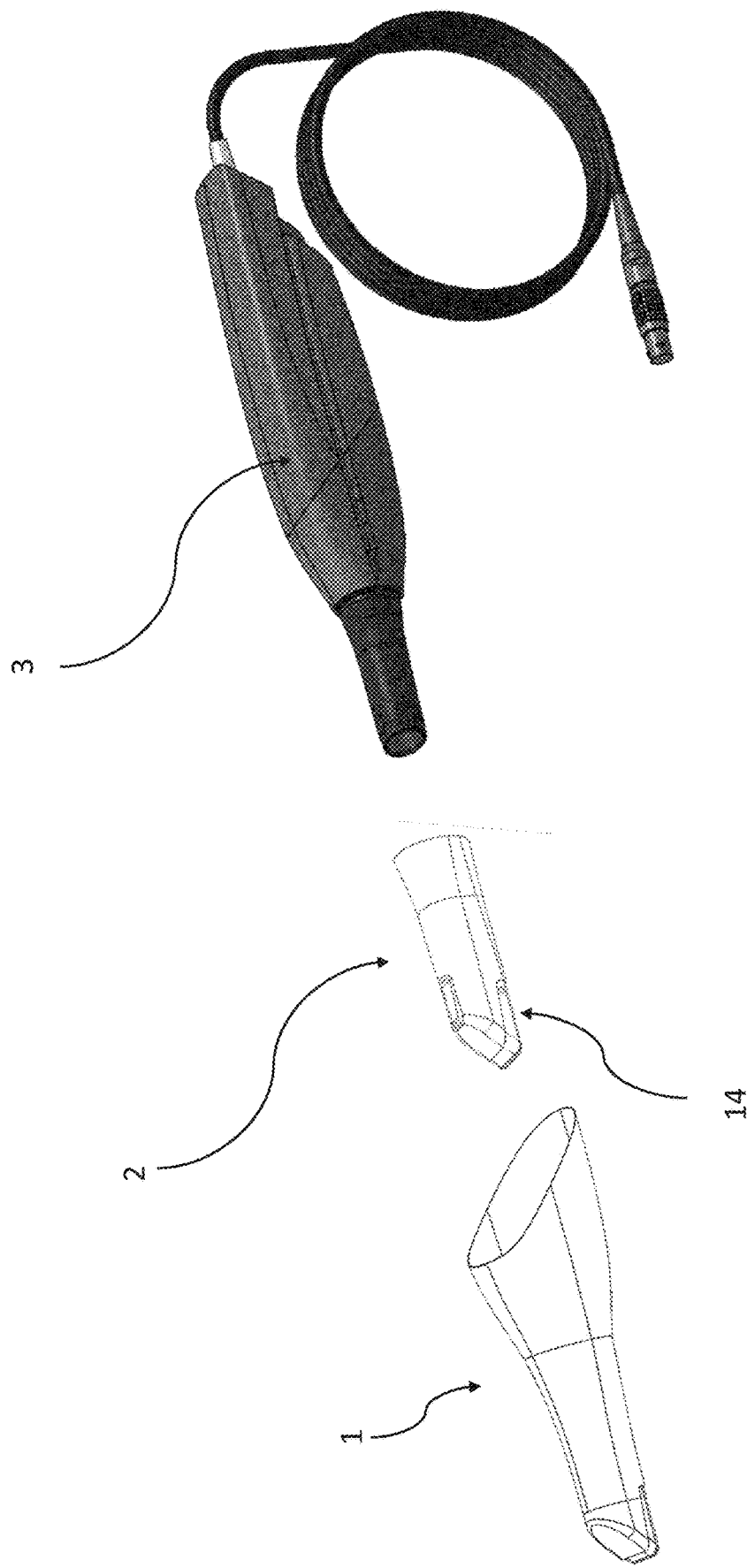
FIG. 10 shows an example of a system comprising a sheath for a tip of a scanning device.

Example 10—A System Comprising a Sheath for a Tip of an Intraoral Scanning Device, Shown as Un-Mounted FIG. 10 shows another example system of an intraoral scanning device (3), comprising: the sheath (1) as shown in FIG. 7, a tip (2) for the scanning device (3) as shown in FIG. 9, wherein the tip (2) is replaceably mountable on the intraoral scanning device (3). The tip (2) comprises an aperture (14) on an optical axis such that light is allowed to exit and to enter the scanning device (3) via the optical axis (10). In FIG. 10, the sheath (1), the tip (2) and the scanning device (3) are shown as unmounted from each other.

Figure 11:
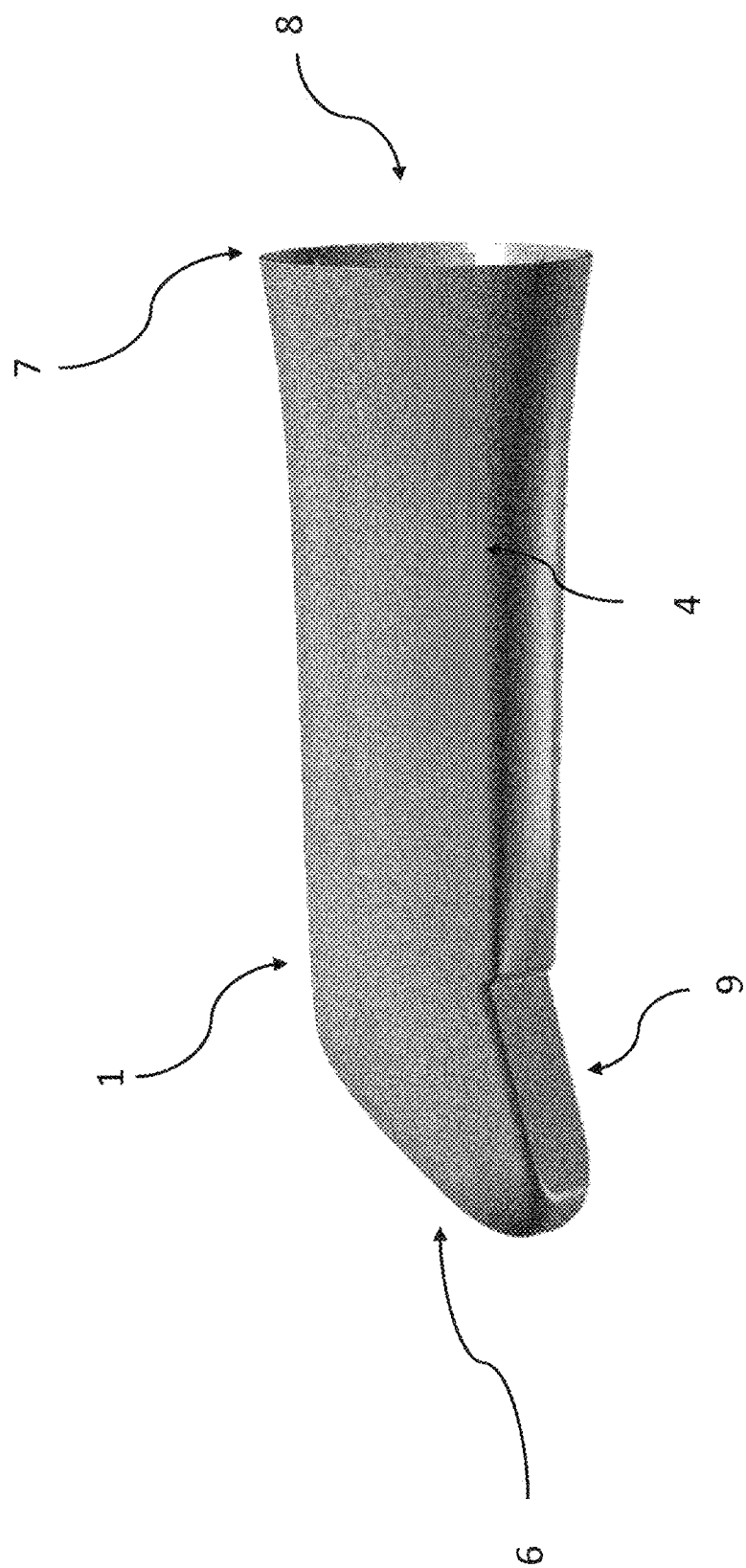
FIG. 11 shows an example of a one-piece molted sheath.

Example 11—A One Piece Semi-Flexible Molted Sheath as Shown from a Perspective View FIG. 11 shows another example of the sheath (1) according to the invention.

FIG. 11 shows a semi-flexible injection molded sheath (1) for a tip (2) of a scanning device (3), comprising: a semi-flexible body (4) comprising a distal end (6) and a proximal end (7). The proximal end (7) comprises an opening (8) that is dimensioned with respect to at least the tip (2) of the scanning device (3), such that the body (4) is able to replaceably fit around at least a part of the tip (2) of the scanning device (3).

The body (4) is molted in a resin composition which is characterized by a high refractive index, a low birefringence, high heat resistance and transparency. The part of the body (4) situated below the tip aperture (14), when mounted on the tip (2), will hence make up an optical window (9) such that the optical window (9) allows for light to exit and to enter the scanning device (3) via an optical axis (10) inside the tip (2) without substantially altering the polarization of said light. The optical window (9) composed by the body (4) is situated such that the optical window (9) comprises a surface normal (11) that deviates from the optical axis (10), whereby internal reflections of the light that exits via the tip (2) is guided away from the optical axis (10). The optical window may contain a hydrophilic coating, such that no fogging of the window will occur when exposed to a humid environment such as the oral cavity.

The invention claimed is:

1. A sheath configured for being replaceably mounted to at least a part of a tip of an intraoral scanning device, thereby being configured to be used in combination with the intraoral scanning device to scan an intraoral cavity, the sheath comprising:
   a hollow body comprising a distal sheath-end, a proximal sheath-end, and a sheathside wall located between the distal sheath-end and the proximal sheath-end,
   wherein the proximal sheath-end forms a sheath-opening that is dimensioned with respect to at least the part of the tip; and
   an optical window mounted to or located in the sheath-side wall near the distal sheathend such that when the sheath is replaceably mounted to at least the part of the tip via the sheath-opening, the optical window covers at least a part of an optical aperture of the tip, wherein the optical window is made of a material configured for not substantially altering the polarization of the light that exits and enters the intraoral scanning device through the optical aperture of the tip and through the optical window to and from the intraoral cavity, thereby ensuring that the scanning device provides substantially the same scan of the intraoral cavity regardless of the sheath being replaceably mounted to at least the part of tip or not; and wherein the optical window has a thickness of more than 400 microns,
   wherein the material is selected to be a polyester resin composition and a polycarbonate resin composition.

2. The sheath according to claim 1, wherein the thickness is more than 600 microns or more than 800 microns.

3. The sheath according to claim 1, wherein the thickness is between 400 microns and 5000 microns.

4. The sheath according to claim 1, wherein the thickness is selected to not substantially deform during the scan of the oral cavity.

5. The sheath according to claim 1, wherein the optical window covers the optical aperture of the tip such that the field-of-view in the intra-oral cavity is maintained.

6. The sheath according to claim 1, wherein the optical window is larger than 10 mm by 10 mm.

7. The sheath according to claim 1, wherein the optical window is planar.

8. The sheath according to claim 1, wherein the optical window comprises a hydrophilic surface.

9. The sheath according to claim 1, wherein the optical window is configured to absorb light in the near infrared domain and/or in the lower visible domain.

10. The sheath according to claim 1, wherein the optical window is injection-molded.

11. The sheath according to claim 1, wherein the optical window is glued, or sealed, or welded into the hollow body.

12. The sheath according to claim 1, wherein the material has a hardness that is selected to withstand the impact of teeth in the intraoral cavity.

13. The sheath according to claim 1, wherein the material is selected to be one or more polymer(s), preferably PMMA and/or cellulose diacetate and/or cellulose triacetate.

14. The sheath according to claim 1, wherein the hollow body is flexible.

15. The sheath according to claim 1, wherein the hollow body is rigid.

16. The sheath according to claim 1, wherein the hollow body is made of one or more polymer(s) or wherein the hollow body is made of a polyester resin composition and a polycarbonate resin composition.

17. The sheath according to claim 1, wherein the hollow body is made of the same material as the optical window.

18. The sheath according to claim 1, wherein the sheath is made of one or more material(s) that is/are adapted to be inserted into the intraoral cavity.

19. The sheath according to claim 1, wherein the sheath is made of one or more material(s) that is/are adapted to be a single-use sheath.

20. A system of an intraoral scanning device, comprising:
   a tip of an intraoral scanning device comprising an optical aperture; and
   a sheath configured for being replaceably mounted to at least a part of the tip of the intraoral scanning device, thereby being configured to be used in combination with the scanning device to scan an oral cavity, the sheath comprising:
   a hollow body comprising, a distal sheath-end, a proximal sheath-end, and a sheath-side wall located between the distal sheath-end and the proximal sheath-end,
   wherein the proximal sheath-end forms a sheath-opening that is dimensioned with respect to at least a part of the tip; and
   an optical window mounted to or located in the sheath-side wall near the distal sheath-end such that when the sheath is replaceably mounted to at least the part of the tip via the sheath-opening, the optical window covers at least a part of an optical aperture of the tip, wherein the optical window is made of a material configured for not substantially altering the polarization of the light that exits and enters the intraoral scanning device trough the optical aperture of the tip and through the optical window to and from the intraoral cavity, thereby ensuring that the scanning device provides substantially the same scan of the intraoral cavity regardless of the sheath being replaceably mounted to at least the part of the tip or not; and wherein the optical window has a thickness of more than 400 microns;
   wherein the sheath is the sheath according to claim 2.

* * * * *